US011751834B2

(12) United States Patent
Kimizuka

(10) Patent No.: US 11,751,834 B2
(45) Date of Patent: Sep. 12, 2023

(54) IMAGE GENERATION APPARATUS, IMAGE GENERATION METHOD, AND INFORMATION STORAGE MEDIUM

(71) Applicant: Rakuten Group, Inc., Tokyo (JP)

(72) Inventor: Joji Kimizuka, Setagaya-ku (JP)

(73) Assignee: Rakuten Group, Inc., Tokyo (JP)

( * ) Notice: Subject to any disclaimer, the term of this patent is extended or adjusted under 35 U.S.C. 154(b) by 0 days.

(21) Appl. No.: 17/715,196

(22) Filed: Apr. 7, 2022

(65) Prior Publication Data
US 2022/0323034 A1 Oct. 13, 2022

(30) Foreign Application Priority Data

Apr. 9, 2021 (JP) ................................. 2021-066408

(51) Int. Cl.
*A61B 6/00* (2006.01)
*G06T 11/00* (2006.01)
(Continued)

(52) U.S. Cl.
CPC .......... *A61B 6/5217* (2013.01); *G06T 11/008* (2013.01); *G06V 10/443* (2022.01);
(Continued)

(58) Field of Classification Search
CPC .... A61B 6/5217; A61B 6/032; G06V 10/443; G06V 40/10; G06V 2201/03; G06V 10/82; G06V 10/457; G06T 11/008
(Continued)

(56) References Cited

U.S. PATENT DOCUMENTS

| 6,198,797 B1 | 3/2001 | Majima et al. |
| 2007/0053485 A1* | 3/2007 | Kobayashi ............. A61B 6/032 378/19 |

(Continued)

FOREIGN PATENT DOCUMENTS

| JP | 2000-093424 A | 4/2000 |
| JP | 2004-81394 A | 3/2004 |

(Continued)

OTHER PUBLICATIONS

Office Action dated May 17, 2022 issued by the Japanese Patent Office in Japanese Application No. 2021-066408.

*Primary Examiner* — Abdul-Samad A Adediran
(74) *Attorney, Agent, or Firm* — Sughrue Mion, PLLC

(57) ABSTRACT

A measurement image acquisition unit 72 acquires a measurement image indicating a measurement value of a predetermined physical quantity for a measurement target including a plurality of types of body tissues. A body tissue image generation unit 74 generates a body tissue image associated with each of the plurality of types of body tissues by executing, for the each of the plurality of types of body tissues, a filtering process corresponding to the each of the plurality of types of body tissues with respect to the measurement image. A masked body tissue image generation unit 78 generates a masked body tissue image associated with a specific type of body tissue by executing, with respect to the body tissue image associated with the specific type of body tissue, a masking process which is based on the body tissue image associated with a different type of body tissue.

9 Claims, 14 Drawing Sheets

(51) Int. Cl.
     *G06V 40/10*      (2022.01)
     *G06V 10/44*      (2022.01)
     *A61B 6/03*      (2006.01)

(52) U.S. Cl.
     CPC .............. *G06V 40/10* (2022.01); *A61B 6/032* (2013.01); *G06V 2201/03* (2022.01)

(58) Field of Classification Search
     USPC .......................................................... 378/19
     See application file for complete search history.

(56) References Cited

U.S. PATENT DOCUMENTS

| | | |
|---|---|---|
| 2009/0087060 A1 | 4/2009 | Omi et al. |
| 2018/0114317 A1* | 4/2018 | Song ...................... G06V 10/82 |
| 2018/0165808 A1* | 6/2018 | Bagci ................... G06V 10/457 |
| 2019/0150859 A1 | 5/2019 | Hamada et al. |
| 2019/0333238 A1 | 10/2019 | Nam et al. |

FOREIGN PATENT DOCUMENTS

| | | |
|---|---|---|
| JP | 2009-82307 A | 4/2009 |
| WO | 2017-179255 A1 | 10/2017 |

\* cited by examiner

IMAGE GENERATION APPARATUS, IMAGE GENERATION METHOD, AND INFORMATION STORAGE MEDIUM

CROSS-REFERENCE TO RELATED APPLICATION

The present application claims priority from Japanese application JP 2021-066408 filed on Apr. 9, 2021, the content of which is hereby incorporated by reference into this application.

BACKGROUND OF THE INVENTION

1. Field of the Invention

The present invention relates to an image generation apparatus, an image generation method, and an information storage medium.

2. Description of the Related Art

In Japanese Patent Application Laid-open No. 2000-93424, there is described a technology of retrieving, on a tomographic image generated by an X-ray CT apparatus, subcutaneous fat pixels and visceral fat pixels that are within a set threshold range of CT values.

Further, there is known a technology of estimating, based on a measurement image indicating a measurement value of a predetermined physical quantity for a measurement target including a plurality of types of body tissues like the above-mentioned tomographic image, a mass of a specific body tissue such as a muscle mass or the like. In this technology, for example, pixels representing a specific body tissue such as a muscle or the like are identified from the measurement image. Then, pixel values of the identified pixels are added up for a plurality of measurement images so that the mass of the specific body tissue such as the muscle mass or the like is estimated.

SUMMARY OF THE INVENTION

When the technology as described in Japanese Patent Application Laid-open No. 2000-93424 is used so that the pixels in the measurement image within the range of the pixel values corresponding to the specific body tissue are identified, pixels representing a different body tissue having a measurement value close to that of the specific body tissue are also erroneously identified as the pixels representing the specific body tissue. As a result, the mass of the specific body tissue is estimated to be larger, and the mass of the specific body tissue cannot be accurately estimated.

In order to prevent this error, it is required to manually remove, through visual inspection, the pixels representing the body tissue that is not the estimation target for a large number of measurement images, which has required time and effort.

The present invention has been made in view of the above-mentioned problem, and has an object to provide an image generation apparatus, an image generation method, and an information storage medium with which pixels representing a specific body tissue can be easily identified.

According to one aspect of the present invention, there is provided an image generation apparatus, including: a measurement image acquirer configured to acquire a measurement image indicating a measurement value of a predetermined physical quantity for a measurement target including a plurality of types of body tissues; a body tissue image generator configured to generate a body tissue image associated with each of the plurality of types of body tissues by executing, for the each of the plurality of types of body tissues, a filtering process corresponding to the each of the plurality of types of body tissues with respect to the measurement image; and a masked body tissue image generator configured to generate a masked body tissue image associated with a specific type of body tissue by executing, with respect to the body tissue image associated with the specific type of body tissue, a masking process which is based on the body tissue image associated with a different type of body tissue.

In one aspect of the present invention, the image generation apparatus further includes a contour identifier configured to identify, based on the body tissue image, a contour of a body tissue in the body tissue image, and the masked body tissue image generator is configured to generate a masked body tissue image associated with a specific type of body tissue by executing, with respect to the body tissue image associated with the specific type of body tissue, a masking process which is based on the contour identified for a different type of body tissue.

Further, in one aspect of the present invention, the body tissue image generator is configured to generate the body tissue image associated with each of a muscle, a bone, and fat.

In this aspect, the masked body tissue image generator may be configured to generate the masked body tissue image associated with the muscle by executing a masking process which is based on the body tissue image associated with the fat with respect to the body tissue image associated with the muscle.

Alternatively, the masked body tissue image generator may be configured to generate the masked body tissue image associated with the muscle by executing a masking process which is based on the body tissue image associated with the fat and the body tissue image associated with the bone with respect to the body tissue image associated with the muscle.

Still alternatively, the masked body tissue image generator may be configured to generate the masked body tissue image associated with the fat by executing a masking process which is based on the body tissue image associated with the bone with respect to the body tissue image associated with the fat.

Further, in one aspect of the present invention, the image generation apparatus further includes a body tissue mass estimator configured to estimate, based on a plurality of the masked body tissue images which are generated for parts different from each other and are associated with the specific type of body tissue, a mass of the specific type of body tissue.

Still further, according to one aspect of the present invention, there is provided an image generation method, including: acquiring a measurement image indicating a measurement value of a predetermined physical quantity for a measurement target including a plurality of types of body tissues; generating a body tissue image associated with each of the plurality of types of body tissues by executing, for the each of the plurality of types of body tissues, a filtering process corresponding to the each of the plurality of types of body tissues with respect to the measurement image; and generating a masked body tissue image associated with a specific type of body tissue by executing, with respect to the body tissue image associated with the specific type of body tissue, a masking process which is based on the body tissue image associated with a different type of body tissue.

Yet further, according to one aspect of the present invention, there is provided an information storage medium having stored thereon a program for causing a computer to execute: acquiring a measurement image indicating a measurement value of a predetermined physical quantity for a measurement target including a plurality of types of body tissues; generating a body tissue image associated with each of the plurality of types of body tissues by executing, for the each of the plurality of types of body tissues, a filtering process corresponding to the each of the plurality of types of body tissues with respect to the measurement image; and generating a masked body tissue image associated with a specific type of body tissue by executing, with respect to the body tissue image associated with the specific type of body tissue, a masking process which is based on the body tissue image associated with a different type of body tissue.

DETAILED DESCRIPTION OF THE INVENTION

At least one embodiment of the present invention is hereinafter described in detail with reference to the drawings.

Figure 1:
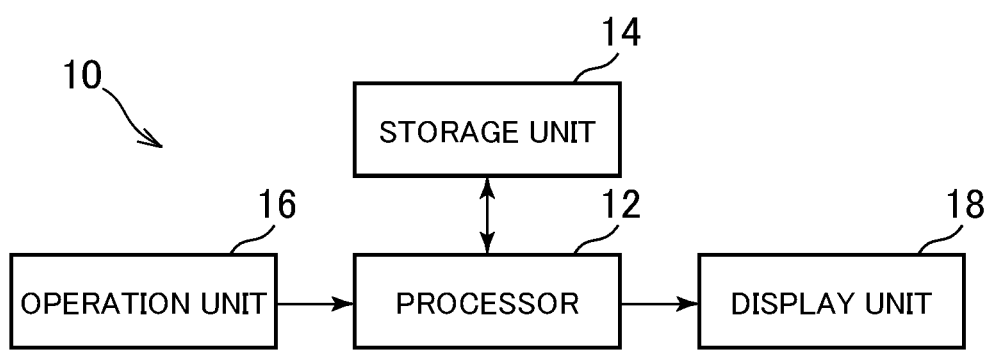
FIG. 1 is a diagram for illustrating an example of a configuration of an image processing apparatus according to at least one embodiment of the present invention.

FIG. 1 is a configuration diagram of an image processing apparatus 10 according to the at least one embodiment. The image processing apparatus 10 according to the at least one embodiment is, for example, a computer, such as a server computer, a personal computer, or the like. As illustrated in FIG. 1, the image processing apparatus 10 according to the at least one embodiment includes, for example, a processor 12, a storage unit 14, an operation unit 16, and a display unit 18.

The processor 12 is, for example, a program control device such as a CPU, which operates in accordance with a program installed in the image processing apparatus 10.

The storage unit 14 is, for example, a storage element such as a ROM or a RAM, a hard disk drive, or a solid-state drive. The storage unit 14 stores, for example, a program to be executed by the processor 12.

The operating unit 16 is, for example, a user interface, such as a keyboard or a mouse, and receives input of an operation performed by a user, and outputs a signal indicating details thereof to the processor 12.

The display unit 18 is a display device such as a liquid crystal display, and displays various images in accordance with instructions issued by the processor 12.

The image processing apparatus 10 may include, for example, a communication interface such as a network board, an optical disc drive for reading an optical disc, such as a DVD-ROM or a Blu-ray (trademark) disc, and a universal serial bus (USB) port.

The image processing apparatus 10 according to the at least one embodiment performs estimation of a mass of a specific type of body tissue included in a given measurement target, such as estimation of a skeletal muscle mass of a human body measured by a CT apparatus or the like.

It is assumed that, when the estimation of the mass of the body tissue is executed, a measurement image 20 (see FIG. 2) indicating a measurement value of a CT value for a cross section of a measurement target such as a human body, which is generated by a CT apparatus, is stored in advance in the image processing apparatus 10. The measurement image 20 is, for example, an image (DICOM image) conforming to Digital Imaging and Communications in Medicine (DICOM).

In the at least one embodiment, it is assumed that, for example, a plurality of measurement images 20 indicating distributions of CT values for partial cross sections which are different from each other for a certain measurement target (for example, partial cross sections which are different from each other in a range of from a thigh bone to an ankle), respectively, are stored in the image processing apparatus 10.

Then, in the at least one embodiment, processes to be described below are executed for each of the plurality of measurement images 20.

First, for a plurality of types of body tissues, filtering processes corresponding to those types of body tissues are executed with respect to the measurement image 20 so that body tissue images associated with those types of body tissues are generated. For example, when three types of body tissues are set as targets, the measurement image 20 is filtered with three types of filters which are different from each other so that three body tissue images are generated.

The body tissue image is, for example, a grayscale image having a range of pixel values indicated by integers of from 0 to 255. Correspondence between the CT value and the pixel value in the body tissue image varies depending on the type of body tissue associated with this body tissue image. Further, in the at least one embodiment, the correspondence between the CT value in the measurement image 20 and the pixel value in the body tissue image is determined in advance for each type of body tissue.

Further, a range of CT values in which a pixel value of 1 or more is set in the body tissue image is also determined in advance for each type of body tissue. Further, a pixel value of 0 is set for a pixel in the body tissue image associated with the pixel in the measurement image 20 indicating a CT value outside of this range.

As described above, in the at least one embodiment, for the plurality of types of body tissues, the body tissue images obtained by extracting the pixels representing those body tissues are generated.

Figure 2:
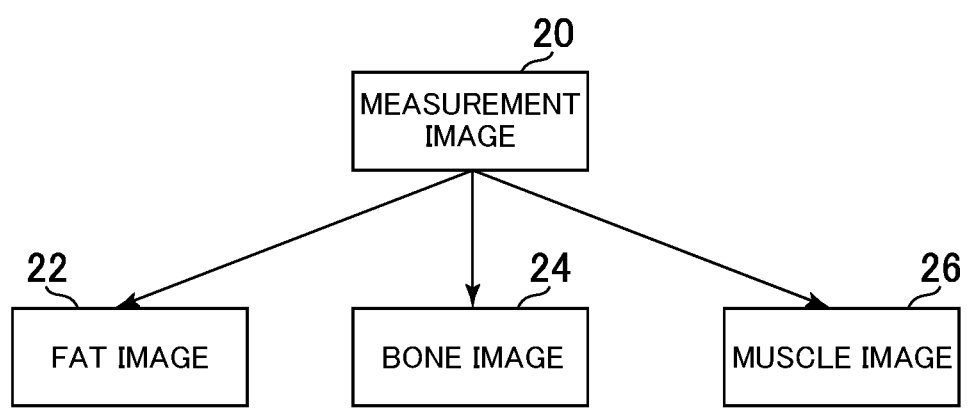
FIG. 2 is a diagram for illustrating an example of generation of a body tissue image.

In the at least one embodiment, for example, as illustrated in FIG. 2, body tissue images associated with fat, a bone, and a muscle, respectively, are generated. In the following, as illustrated in FIG. 2, a body tissue image obtained by extracting pixels representing the fat is referred to as "fat image 22." Further, a body tissue image obtained by extracting pixels representing the bone is referred to as "bone image 24." Further, a body tissue image obtained by extracting pixels representing the muscle is referred to as "muscle image 26."

For example, the fat image 22 obtained by extracting pixels within a predetermined CT value range (hereinafter referred to as "fat range") associated with the fat is generated from the measurement image 20. In this case, the pixel value of 0 is set for pixels in the fat image 22 associated with the pixels in the measurement image 20 indicating the CT values outside of this fat range.

Further, the bone image 24 obtained by extracting pixels within a predetermined CT value range (hereinafter referred to as "bone range") associated with the bone is generated from the measurement image 20. In this case, the pixel value of 0 is set for pixels in the bone image 24 associated with the pixels in the measurement image 20 indicating the CT values outside of this bone range.

Still further, the muscle image 26 obtained by extracting pixels within a predetermined CT value range (hereinafter referred to as "muscle range") associated with the muscle is generated from the measurement image 20. In this case, the pixel value of 0 is set for pixels in the muscle image 26 associated with the pixels in the measurement image 20 indicating the CT values outside of this muscle range.

Figure 3:
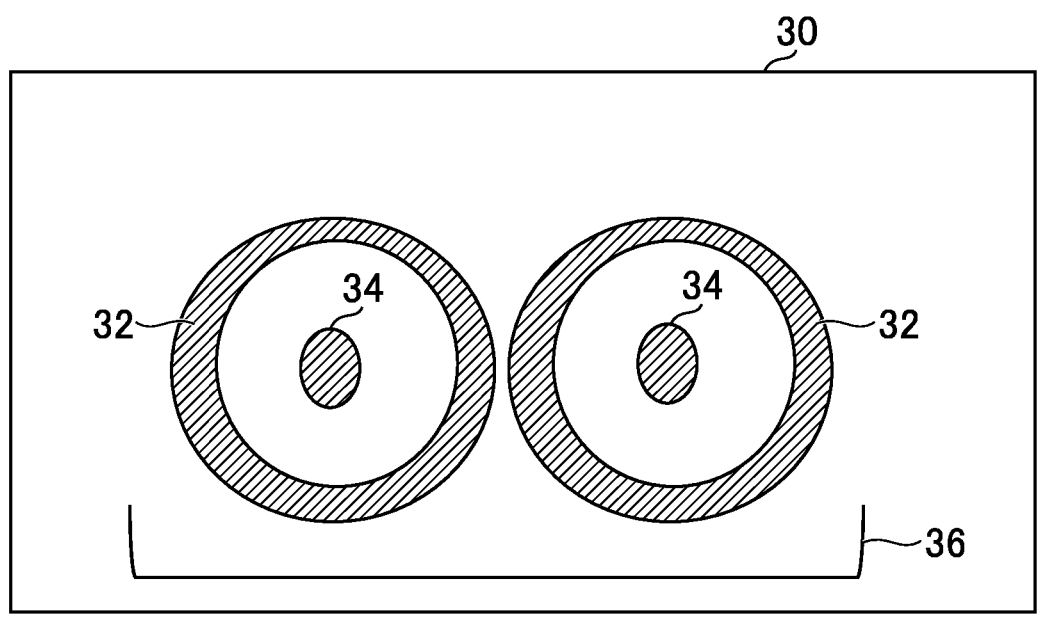
FIG. 3 is a view for schematically illustrating an example of a binarized fat image.

In addition, in the at least one embodiment, binarization for discriminating the pixel having the pixel value of 0 and the pixel having the pixel value of 1 or more is executed with respect to the fat image 22. In this manner, a binarized fat image 30 schematically illustrated as an example in FIG. 3 is generated. For example, the binarized fat image 30 can be generated through use of threshold( ) of the OpenCV function.

For example, the pixel value of 0 is set for pixels in the binarized fat image 30 associated with the pixels each having the pixel value of 0 in the fat image 22, and the pixel value of 1 is set for pixels in the binarized fat image 30 associated with the pixels each having the pixel value of 1 or more in the fat image 22. In the example of FIG. 3, a hatched region corresponds to a region of the pixels each having the pixel value of 1, and an unhatched region corresponds to a region of the pixels each having the pixel value of 0.

In the binarized fat image 30, the pixel value of 1 is set for the pixels representing the fat. FIG. 3 shows a region corresponding to the fat as a fat region 32.

Further, among objects that are not the fat, there are some objects for which the pixel value of 1 is set in the binarized fat image 30. For example, the pixel value of 1 is sometimes set for pixels representing a bone, bone marrow, and the like in the binarized fat image 30. FIG. 3 shows a region in which the pixel value of 1 is set even for body tissues that are not the fat, such as the bone, the bone marrow, and the like, as an erroneous detection fat region 34. Further, the pixel value of 1 is sometimes set for pixels representing a CT bed in the binarized fat image 30. FIG. 3 shows a linear pixel group representing the CT bed as a CT bed part 36.

Figure 4:
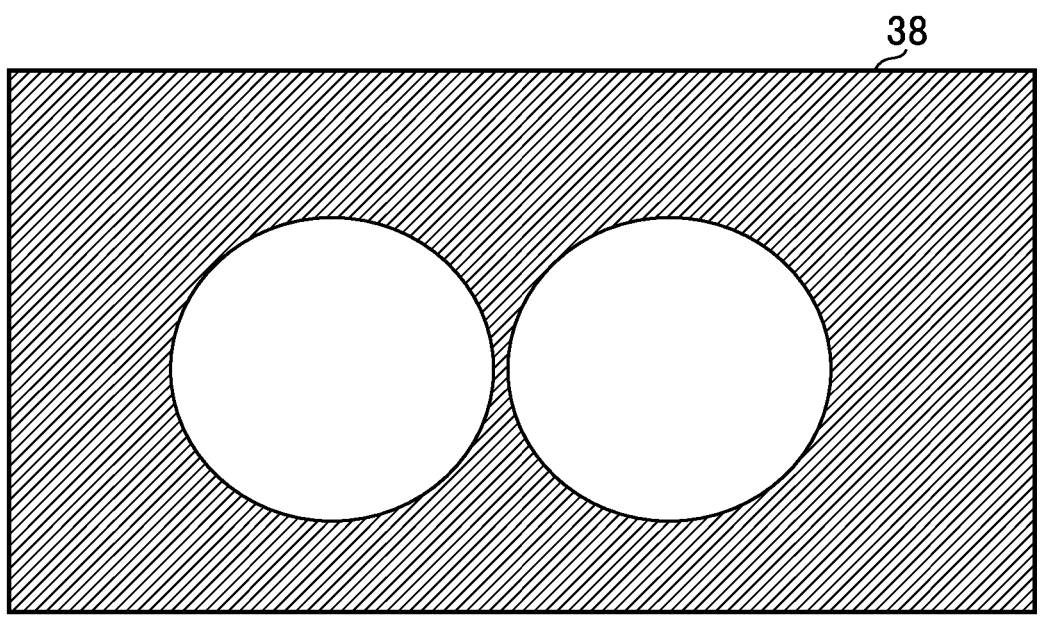
FIG. 4 is a view for schematically illustrating an example of a skin mask image.

In addition, in the at least one embodiment, a skin mask image 38 exemplified in FIG. 4 is generated based on the binarized fat image 30 so that an outer region and an inner side of skin in the measurement target are distinguished from each other. In the skin mask image 38 illustrated in FIG. 4, the pixel value of 1 is set for pixels corresponding to the outer side of the skin, and the pixel value of 0 is set for pixels corresponding to the inner side of the skin. In the example of FIG. 4, a hatched region corresponds to a region of the pixels each having the pixel value of 1, and an unhatched region corresponds to a region of the pixels each having the pixel value of 0.

For example, through use of findContours( ) of the OpenCV function, a first hierarchy contour (outermost contour among the nested contours) can be extracted. Then, in the at least one embodiment, for example, in the extracted at least one first hierarchy contour, a first hierarchy contour being a seamless contour and having the largest area is identified. Then, at least one first hierarchy contour having an area of ¼ or more of the area of the first hierarchy contour being the seamless contour and having the largest area is identified as a skin contour.

Then, for example, the skin mask image 38 exemplified in FIG. 4 in which the pixel value of 1 is set for the region on the outer side of the identified skin contour, and the pixel value of 0 is set for the region on the inner side of the identified skin contour is generated.

Figure 5:
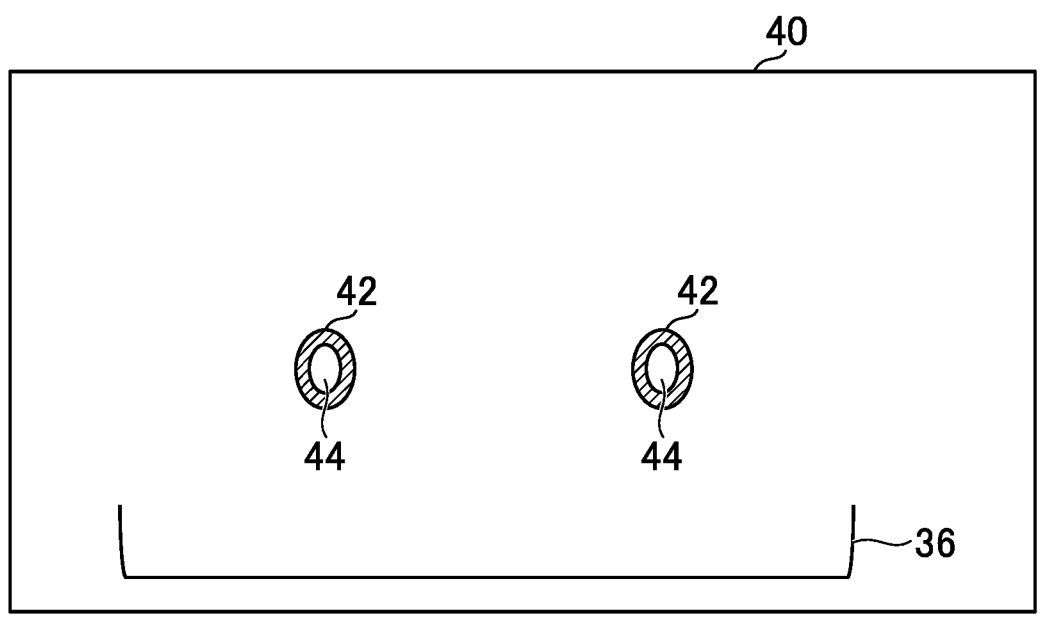
FIG. 5 is a view for schematically illustrating an example of a binarized bone image.

In addition, in the at least one embodiment, binarization for discriminating the pixel having the pixel value of 0 and the pixel having the pixel value of 1 or more is executed with respect to the bone image 24. In this manner, a binarized bone image 40 schematically illustrated as an example in FIG. 5 is generated. For example, the binarized bone image 40 can be generated through use of threshold( ) of the OpenCV function.

For example, the pixel value of 0 is set for pixels in the binarized bone image 40 associated with the pixels each having the pixel value of 0 in the bone image 24, and the pixel value of 1 is set for pixels in the binarized bone image 40 associated with the pixels each having the pixel value of 1 or more in the bone image 24. In the example of FIG. 5, a hatched region corresponds to a region of the pixels each having the pixel value of 1, and an unhatched region corresponds to a region of the pixels each having the pixel value of 0.

In the example of FIG. 5, the hatched ring-shaped region corresponds to a region of pixels representing the bone (hereinafter referred to as "bone region 42"), and the unhatched region on the inner side of the bone region 42 corresponds to a region of pixels representing the bone marrow (hereinafter referred to as "bone marrow region 44").

Further, also in the binarized bone image 40 illustrated in FIG. 5, similarly to the binarized fat image 30 illustrated in FIG. 3, the pixel value of 1 is sometimes set for the pixels representing the CT bed. FIG. 5 also shows the linear pixel group representing the CT bed as the CT bed part 36.

Figure 6:
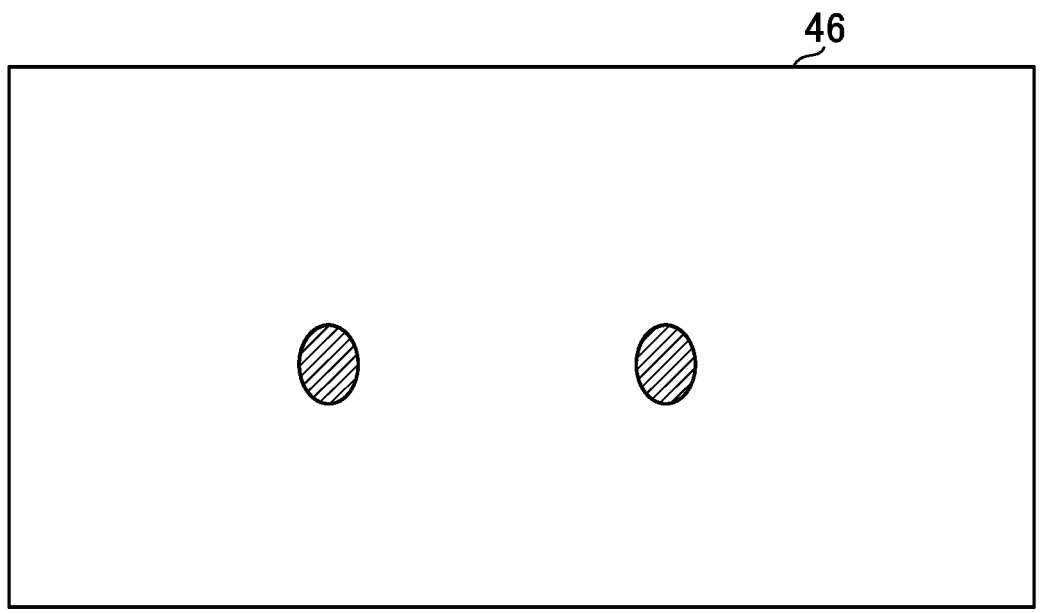
FIG. 6 is a view for schematically illustrating an example of a bone mask image.

In addition, in the at least one embodiment, a bone mask image 46 exemplified in FIG. 6 is generated based on the binarized bone image 40 so that a region on an inner side of the contour of the bone and a region other than this region are distinguished from each other. In the bone mask image 46 illustrated in FIG. 6, the pixel value of 1 is set for pixels corresponding to the inner side of the contour of the bone, and the pixel value of 0 is set for pixels corresponding to the outer side of the contour of the bone. In the example of FIG. 6, a hatched region corresponds to a region of the pixels each having the pixel value of 1, and an unhatched region corresponds to a region of the pixels each having the pixel value of 0.

As described above, for example, through use of findContours( ) of the OpenCV function, the first hierarchy contour can be extracted. Then, in the at least one embodiment, for example, the first hierarchy contour extracted as described above is identified as a bone contour. Then, the bone mask image 46 exemplified in FIG. 6 in which the pixel value of 1 is set for the region on the inner side of the identified bone contour, and the pixel value of 0 is set for the region on the outer side of the identified bone contour is generated.

Figure 7:
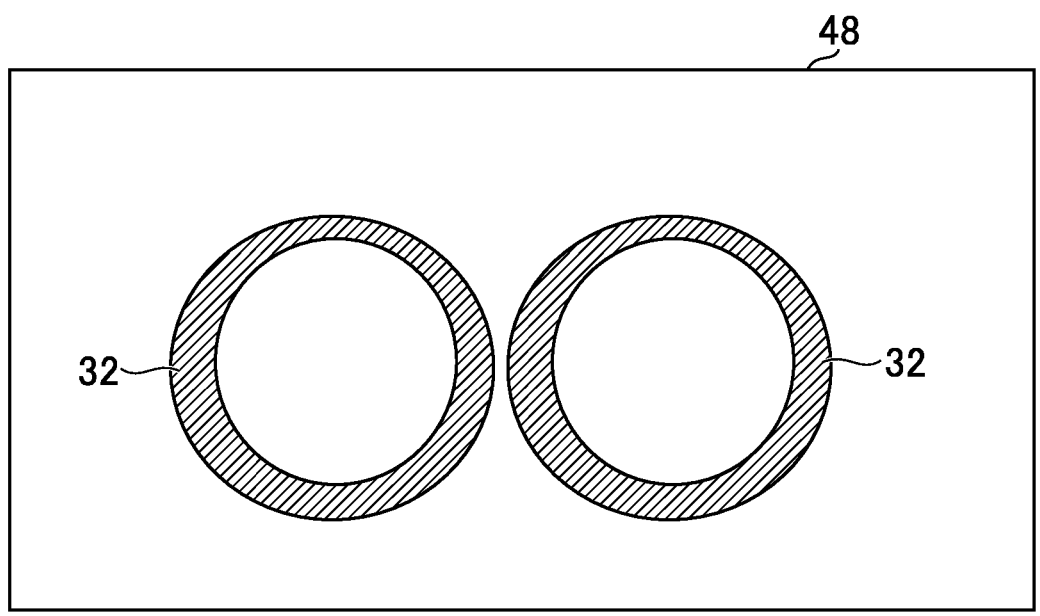
FIG. 7 is a view for schematically illustrating an example of a masked fat image.

In addition, a masking process which is based on the skin mask image 38 and the bone mask image 46 is executed with respect to the fat image 22 so that a masked fat image 48 schematically illustrated as an example in FIG. 7 is generated. In this case, for example, the masked fat image 48 is generated by executing, with respect to the fat image 22, a process of changing the pixel values of the pixels associated with the pixels each having the pixel value of 1 in the skin mask image 38 and the pixels each having the pixel value of 1 in the bone mask image 46 to 0. In the masked fat image 48 illustrated in FIG. 7, a hatched region corresponds to a region of the pixels each having the pixel value of 1 or more, and an unhatched region corresponds to a region of the pixels each having the pixel value of 0.

In this manner, the masked fat image 48 obtained by removing the erroneous detection fat region 34 and the CT bed part 36 from the fat image 22 (masked fat image 48 in which the pixel values of the erroneous detection fat region 34 and the CT bed part 36 have become 0) is generated. In the masked fat image 48, the fat region 32 representing the fat can be more accurately extracted as compared to the fat image 22.

Figure 8:
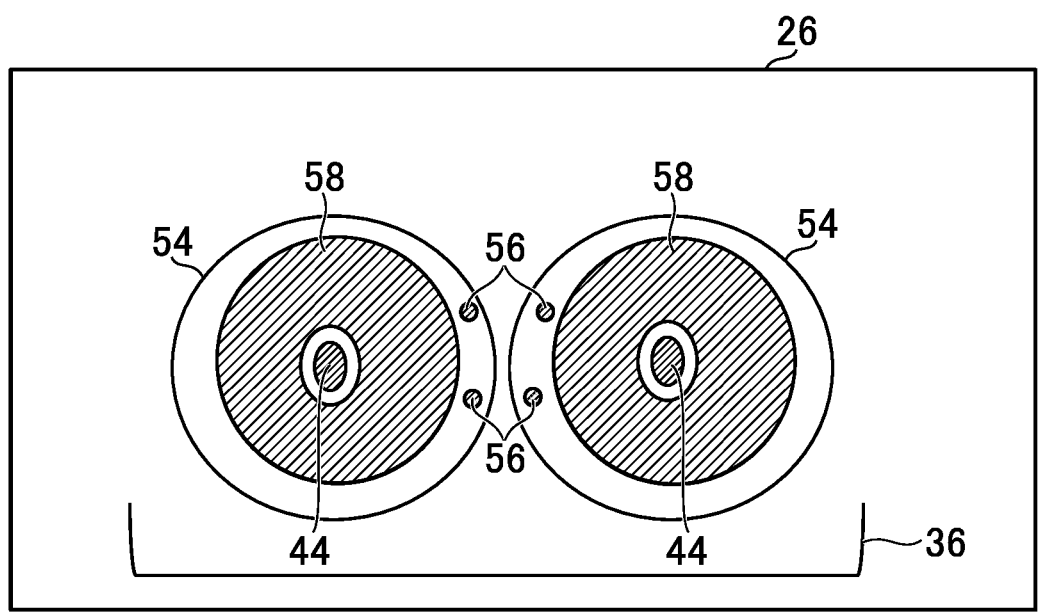
FIG. 8 is a view for schematically illustrating an example of a muscle image.
Figure 9:
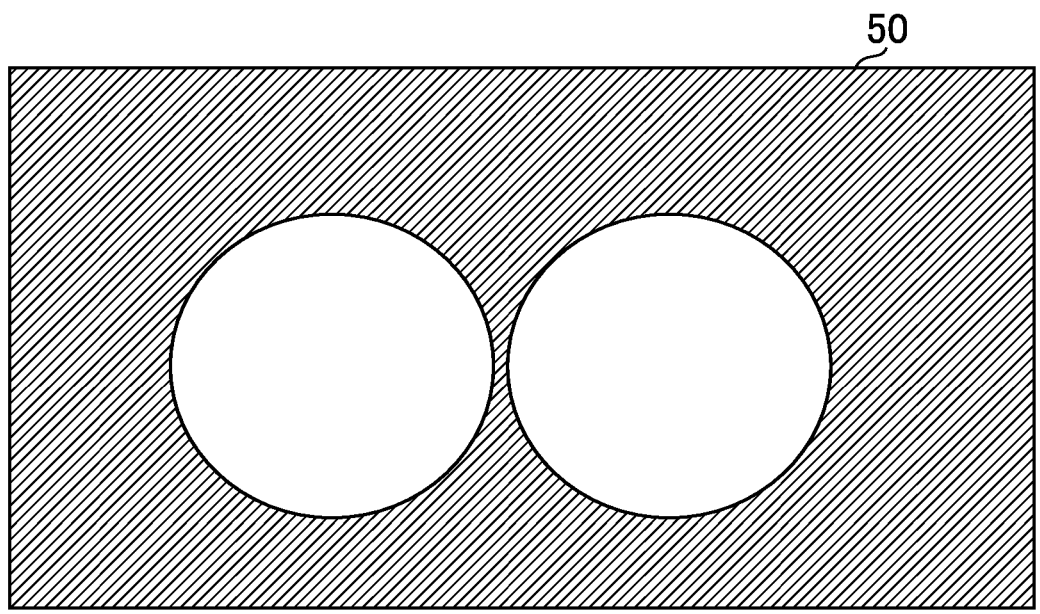
FIG. 9 is a view for schematically illustrating an example of a reduced skin mask image.
Figure 10:
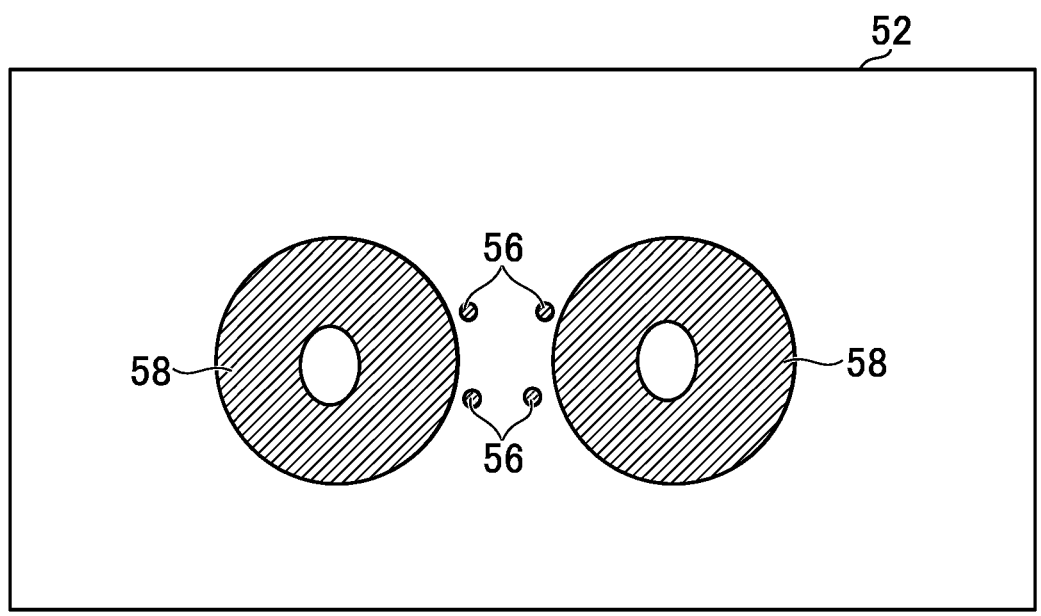
FIG. 10 is a view for schematically illustrating an example of an intermediate masked muscle image.

In addition, in the at least one embodiment, for example, a masking process which is based on the bone mask image 46 exemplified in FIG. 6 and a reduced skin mask image 50 exemplified in FIG. 9 is executed with respect to the muscle image 26 schematically illustrated as an example in FIG. 8 so that an intermediate masked muscle image 52 schematically illustrated as an example in FIG. 10 is generated.

In the example of FIG. 8, a hatched region corresponds to a region of the pixels each having the pixel value of 1 or more, and an unhatched region corresponds to a region of the pixels each having the pixel value of 0.

Among objects that are not the muscle, there are some objects for which the pixel value of 1 or more is set in the muscle image 26. For example, the pixel value of 1 or more is sometimes set for pixels representing the CT bed in the muscle image 26. FIG. 8 shows a linear pixel group representing the CT bed as the CT bed part 36. Further, for example, the pixel value of 1 or more is sometimes set for pixels representing skin in the muscle image 26. FIG. 8 shows a circular pixel group representing the skin as a skin part 54.

Further, for example, the pixel value of 1 or more is sometimes set for pixels representing a blood vessel such as a vein or the like in the muscle image 26. FIG. 8 shows a region corresponding to the blood vessel such as the vein or the like as a blood vessel region 56. Further, for example, the pixel value of 1 or more is sometimes set for pixels representing the bone marrow in the muscle image 26. FIG. 8 shows a region corresponding to the bone marrow as the bone marrow region 44.

In addition, as a matter of course, the pixel value of 1 or more is set for pixels representing the muscle in the muscle image 26. FIG. 8 shows a region corresponding to the muscle as a muscle region 58.

FIG. 9 is a view for schematically illustrating an example of the reduced skin mask image 50. The reduced skin mask image 50 is, for example, an image generated by eroding, through use of erode( ) of the OpenCV function, the region having the pixel value of 0 of the skin mask image 38 illustrated in FIG. 4 a predetermined number of times (for example, two or three times). In this manner, the reduced skin mask image 50 which is an image in which the region having the pixel value of 0 is a little smaller than that of the skin mask image 38 is generated.

Then, a masking process which is based on the bone mask image 46 and the reduced skin mask image 50 is executed with respect to the muscle image 26 so that the intermediate masked muscle image 52 exemplified in FIG. 10 is generated. In this case, for example, the intermediate masked muscle image 52 is generated by executing, with respect to the muscle image 26, a process of changing the pixel values of the pixels associated with the pixels each having the pixel value of 1 in the bone mask image 46 and the pixels each having the pixel value of 1 in the reduced skin mask image 50 to 0. In the intermediate masked muscle image 52 illustrated in FIG. 10, a hatched region corresponds to a region of the pixels each having the pixel value of 1 or more, and an unhatched region corresponds to a region of the pixels each having the pixel value of 0.

In this manner, the intermediate masked muscle image 52 obtained by removing the CT bed part 36, the skin part 54, and the bone marrow region 44 from the muscle image 26 (intermediate masked muscle image 52 in which the pixel values of the CT bed part 36, the skin part 54, and the bone marrow region 44 have become 0) is generated. In the intermediate masked muscle image 52, the muscle region 58 representing the muscle can be more accurately extracted as compared to the muscle image 26, but the blood vessel region 56 is still left without being removed.

Figure 11:
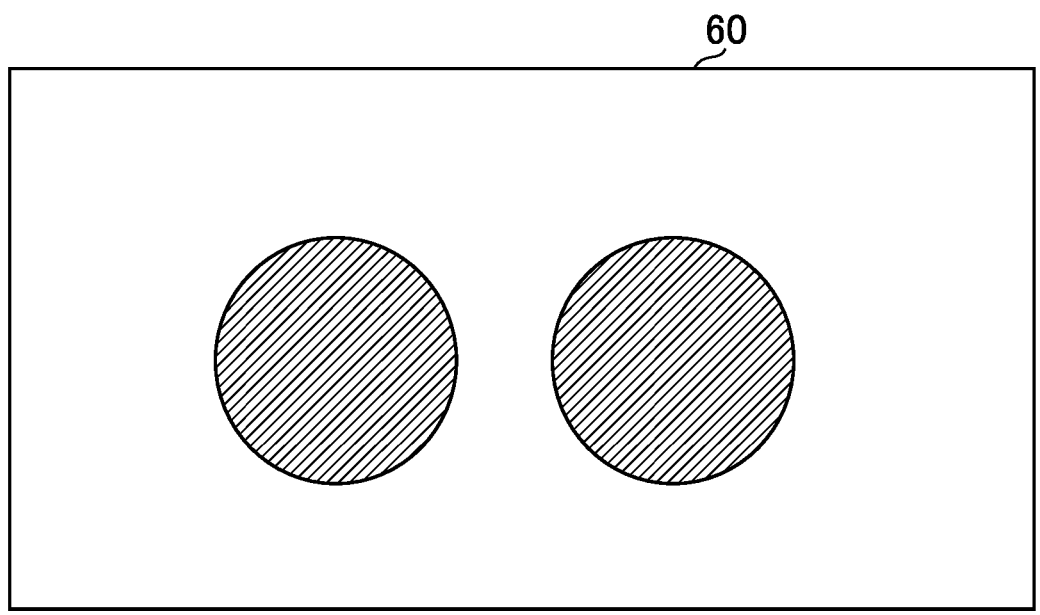
FIG. 11 is a view for schematically illustrating an example of a comparison image.

In view of the above, in the at least one embodiment, a comparison image 60 exemplified in FIG. 11 is generated based on the masked fat image 48 schematically illustrated as an example in FIG. 7.

In this case, for example, an image in which the pixel value of 0 is set for pixels associated with, in the masked fat image 48, the pixels in the region on the outer side of the skin and the pixels which are located on the inner side of the skin and each have the pixel value of 1 or more, and the pixel value of 1 is set for pixels associated with the pixels which are located on the inner side of the skin and each have the pixel value of 0 is generated. For example, this image can be generated through use of threshold( ) of the OpenCV function.

Then, for example, the contour is extracted from the image generated as described above through use of findContours( ) of the OpenCV function.

Then, a convex hull of the extracted contour is identified for each of a left-half region and a right-half region of the generated image. In the identification of the convex hull, for example, a process such as calculation of an arc length (perimeter) using arclength( ) of the OpenCV function, calculation of an approximate contour using approxPoly DP( ) or the like may be executed. In this case, for example, it is assumed that two convex hulls are identified. In the at least one embodiment, a larger number of small convex hulls may be identified.

Then, the comparison image 60 exemplified in FIG. 11 in which the pixel value of 1 is set for pixels on the inner side of the identified convex hull, and the pixel value of 0 is set for pixels on the outer side of the identified convex hull is generated. It is considered that, in the comparison image 60, the contour of the region for which the pixel value of 1 is set substantially represents a fascia or the vicinity of the fascia.

Figure 12:
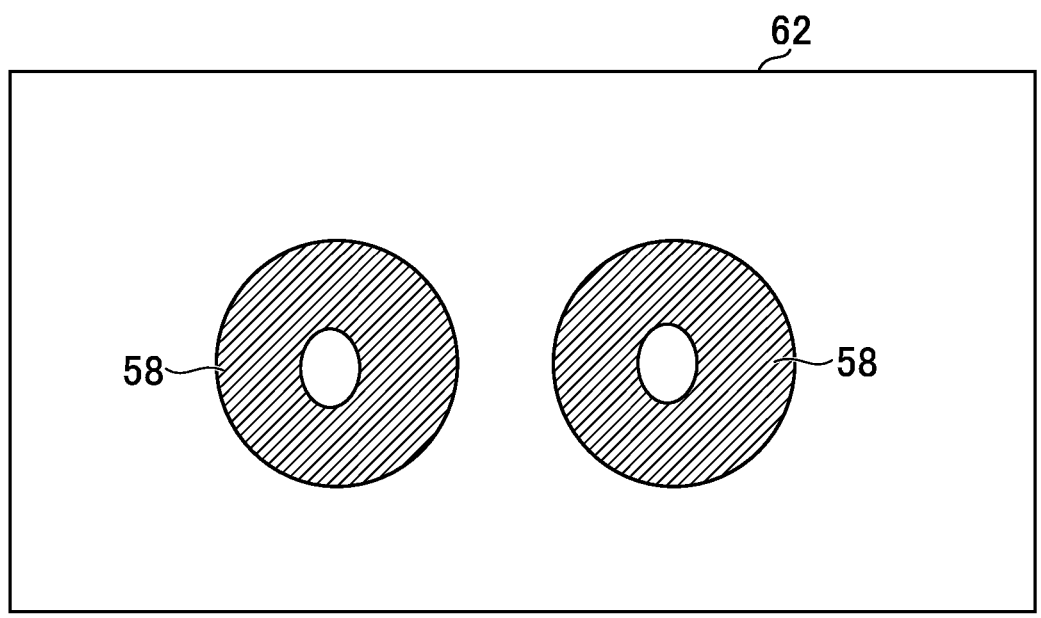
FIG. 12 is a view for schematically illustrating an example of a masked muscle image.

Then, a masking process which is based on the comparison image 60 is executed with respect to the intermediate masked muscle image 52 so that a masked muscle image 62 schematically illustrated as an example in FIG. 12 is generated. In this case, for example, the masked muscle image 62 illustrated in FIG. 12 is generated by executing, with respect to the intermediate masked muscle image 52, a process of changing the pixel values of the pixels associated with the pixels each having the pixel value of 0 in the comparison image 60 to 0. In the masked muscle image 62 illustrated in FIG. 12, a hatched region corresponds to a region of the pixels each having the pixel value of 1 or more, and an unhatched region corresponds to a region of the pixels each having the pixel value of 0.

In this manner, the masked muscle image 62 obtained by removing the region (in the example of FIG. 10, the blood vessel region 56) representing the body tissue present between the muscle and the skin (for example, the blood vessel such as the vein or the like) from the intermediate masked muscle image 52 (masked muscle image 62 in which the pixel value of the blood vessel region 56 has become 0) is generated. In the masked muscle image 62, the muscle region 58 representing the muscle can be more accurately extracted as compared to the intermediate masked muscle image 52.

In the at least one embodiment, for example, the processes described above are executed with respect to a plurality of measurement images 20 so that the masked muscle image 62 associated with each of the plurality of measurement images 20 is generated.

Then, for example, a skeletal muscle mass measurement automation technology such as a publicly known skeletal muscle mass measurement automation technology or the like is used based on the masked muscle images 62 generated as described above so that the skeletal muscle mass is estimated. For example, a total of the pixel values in the plurality of masked muscle images 62 may be multiplied by a predetermined coefficient so that an estimated value of the skeletal muscle mass is calculated. As another example, a total of the number of pixels each having the pixel value of 1 or more in the plurality of masked muscle images 62 may be multiplied by a predetermined coefficient so that the estimated value of the skeletal muscle mass is calculated.

When the skeletal muscle mass is estimated based on the muscle images 26, pixels representing a different body tissue or object having a CT value close to that of the muscle in the muscle image 26 are also treated as a part of the pixels representing the muscle. In the above-mentioned example, the pixels in the CT bed part 36, the bone marrow region 44, the skin part 54, and the blood vessel region 56 are treated as a part of the pixels representing the muscle. Accordingly, the skeletal muscle mass is estimated to be larger, and the skeletal muscle mass cannot be accurately estimated.

In this case, when the pixels representing the body tissue or the object other than the muscle are manually removed from the muscle image 26 through visual inspection, time and effort are required.

In the at least one embodiment, as described above, pixels representing a specific body tissue such as a muscle or the like can be easily identified from the measurement image 20. Further, in the at least one embodiment, the skeletal muscle mass is estimated based on the masked muscle images 62 each obtained by removing the CT bed part 36, the skin part 54, and the bone marrow region 44 from the muscle image 26, and hence the skeletal muscle mass can be accurately estimated.

Now, functions of the image processing apparatus 10 according to the at least one embodiment and a process to be executed by the image processing apparatus 10 according to the at least one embodiment are further described.

Figure 13:
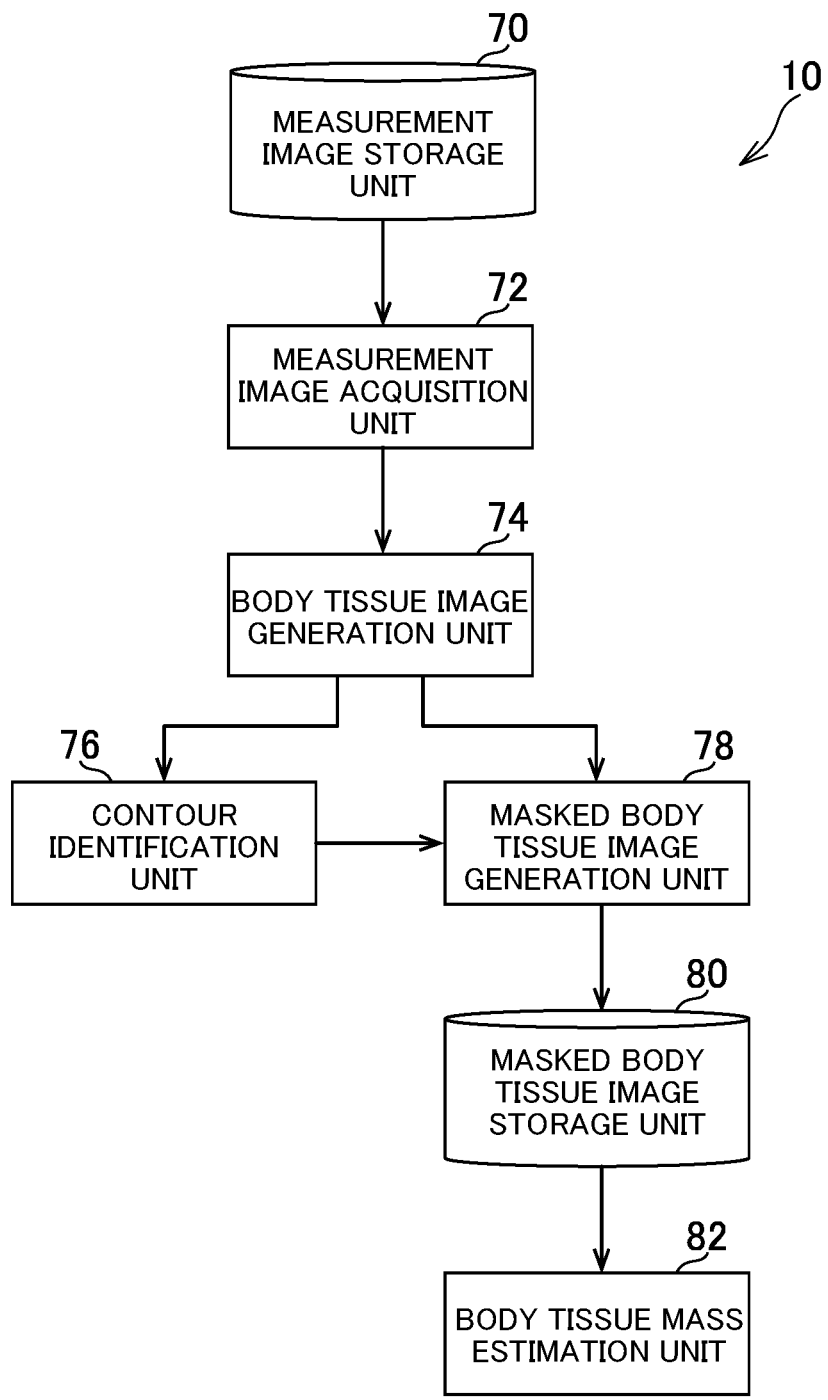
FIG. 13 is a functional block diagram for illustrating an example of functions of the image processing apparatus according to the at least one embodiment of the present invention.

FIG. 13 is a functional block diagram for illustrating an example of functions to be implemented by the image processing apparatus 10 according to the at least one embodiment. It is not required to implement all of the functions illustrated in FIG. 13 by the image processing apparatus 10 according to the at least one embodiment. Further, functions other than the functions illustrated in FIG. 13 may be implemented by the image processing apparatus 10 according to the at least one embodiment.

As illustrated in FIG. 13, the image processing apparatus 10 according to the at least one embodiment functionally includes, for example, a measurement image storage unit 70, a measurement image acquisition unit 72, a body tissue image generation unit 74, a contour identification unit 76, a masked body tissue image generation unit 78, a masked body tissue image storage unit 80, and a body tissue mass estimation unit 82.

The measurement image storage unit 70 and the masked body tissue image storage unit 80 are mainly implemented by the storage unit 14. The measurement image acquisition unit 72, the body tissue image generation unit 74, the contour identification unit 76, the masked body tissue image generation unit 78, and the body tissue mass estimation unit 82 are mainly implemented by the processor 12.

The above-mentioned functions may be implemented by executing, by the processor 12, a program that is installed in the image processing apparatus 10, which is a computer, and that includes instructions corresponding to the above-mentioned functions. Further, this program may be supplied to the image processing apparatus 10 via a computer-readable information storage medium, such as an optical disc, a magnetic disk, a magnetic tape, a magneto-optical disc, or the like, or via the Internet or the like.

In the at least one embodiment, the measurement image storage unit 70 stores, for example, the measurement image 20 indicating a measurement value (in the above-mentioned example, the CT value) of a predetermined physical quantity for a measurement target including a plurality of types of body tissues.

In the at least one embodiment, the measurement image acquisition unit 72 acquires, for example, the measurement image 20 indicating the measurement value (in the above-mentioned example, the CT value) of the predetermined physical quantity for the measurement target including the plurality of types of body tissues. The measurement image acquisition unit 72 may acquire the measurement image 20 stored in the measurement image storage unit 70.

In the at least one embodiment, the body tissue image generation unit 74 executes, for example, for the plurality of types of body tissues, filtering processes corresponding to those types of body tissues with respect to the measurement image 20 so that body tissue images associated with those types of body tissues are generated.

The body tissue image generation unit 74 generates, for example, as described above, based on the measurement image 20, the fat image 22 being the body tissue image associated with the fat, the bone image 24 being the body tissue image associated with the bone, and the muscle image 26 being the body tissue image associated with the muscle.

In the at least one embodiment, the contour identification unit 76 identifies, for example, based on the body tissue image, a contour of the body tissue in this body tissue image. In this case, the contour identification unit 76 may generate a mask image being an image representing the identified contour.

The contour identification unit 76 generates, for example, the skin mask image 38 and the reduced skin mask image 50 based on the fat image 22.

Further, the contour identification unit 76 generates, for example, the bone mask image 46 based on the bone image 24.

Still further, the contour identification unit 76 generates, for example, the comparison image 60 based on the fat image 22.

In the at least one embodiment, the masked body tissue image generation unit 78 executes, for example, with respect to the body tissue image associated with a specific type of body tissue, a masking process which is based on the body tissue image associated with a different type of body tissue. Further, in the at least one embodiment, the masked body tissue image generation unit 78 executes, for example, this masking process so that the masked body tissue image associated with this specific type of body tissue is generated.

The masked body tissue image generation unit 78 may execute, with respect to the body tissue image associated with the specific type of body tissue, a masking process which is based on the contour identified for the different type of body tissue so that the masked body tissue image associated with this specific type of body tissue is generated.

For example, the masked body tissue image generation unit 78 may execute the masking process which is based on the fat image 22 with respect to the muscle image 26 so that the masked muscle image 62 being the masked body tissue image associated with the muscle is generated. Further, the masked body tissue image generation unit 78 may execute the masking process which is based on the fat image 22 and the bone image 24 with respect to the muscle image 26 so that the masked muscle image 62 being the masked body tissue image associated with the muscle is generated. For example, as described above, the masked body tissue image generation unit 78 may execute the masking process which is based on the bone mask image 46, the reduced skin mask image 50, and the comparison image 60 with respect to the muscle image 26 so that the masked muscle image 62 is generated.

Further, the masked body tissue image generation unit 78 may execute the masking process which is based on the bone image 24 with respect to the fat image 22 so that the masked fat image 48 being the masked body tissue image associated with the fat is generated. For example, as described above, the masked body tissue image generation unit 78 may execute the masking process which is based on the skin mask image 38 and the bone mask image 46 with respect to the fat image 22 so that the masked fat image 48 is generated.

Still further, in the at least one embodiment, the masked body tissue image generation unit 78 stores, for example, the generated masked body tissue image into the masked body tissue image storage unit 80.

In the at least one embodiment, the masked body tissue image storage unit 80 stores, for example, the masked body tissue image generated by the masked body tissue image generation unit 78.

In the at least one embodiment, the body tissue mass estimation unit 82 estimates, for example, based on the plurality of masked body tissue images each associated with the specific type of body tissue, which are generated for parts different from each other, a mass of this specific type of body tissue. For example, as described above, the body tissue mass estimation unit 82 may estimate the skeletal muscle mass based on the masked muscle images 62.

Further, the body tissue mass estimation unit 82 may estimate, for example, a fat mass based on the masked fat images 48. Further, the body tissue mass estimation unit 82 may estimate, for example, a bone mass based on the bone images 24.

Figure 14:
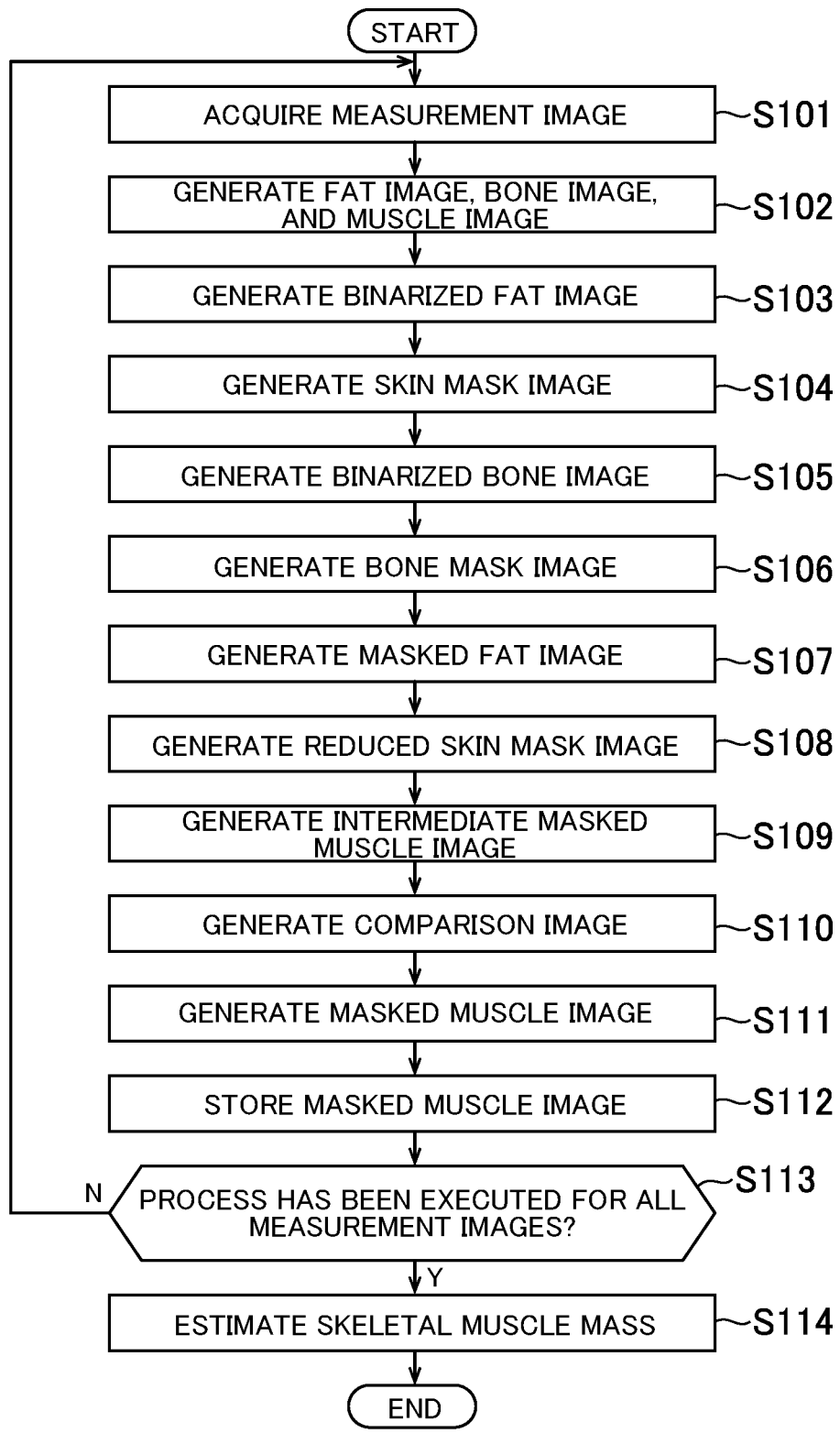
FIG. 14 is a flow chart for illustrating an example of flow of a process to be performed by the image processing apparatus according to the at least one embodiment of the present invention.

Now, an example of flow of a skeletal muscle mass estimation process to be performed by the image processing apparatus 10 according to the at least one embodiment is described with reference to the flow chart exemplified in FIG. 14. In the process illustrated in this process example, it is assumed that a plurality of measurement images 20 indicating distributions of CT values for partial cross sections which are different from each other for a certain measurement target, respectively, are stored in advance in the measurement image storage unit 70.

First, the measurement image acquisition unit 72 acquires, from among the measurement images 20 stored in the measurement image storage unit 70, one measurement image 20 for which the process steps of Step S102 to Step S112 have yet to be executed (Step S101).

Then, the body tissue image generation unit 74 generates the fat image 22, the bone image 24, and the muscle image 26 based on the measurement image 20 acquired in the process step of Step S101 (Step S102).

Then, the contour identification unit 76 generates the binarized fat image 30 based on the fat image 22 generated in the process step of Step S102 (Step S103).

Then, the contour identification unit 76 generates the skin mask image 38 based on the binarized fat image 30 generated in the process step of Step S103 (Step S104).

Then, the contour identification unit 76 generates the binarized bone image 40 based on the bone image 24 generated in the process step of Step S102 (Step S105).

Then, the contour identification unit 76 generates the bone mask image 46 based on the binarized bone image 40 generated in the process step of Step S105 (Step S106).

Then, the masked body tissue image generation unit 78 executes, with respect to the fat image 22 generated in the process step of Step S102, a masking process which is based on the skin mask image 38 generated in the process step of Step S104 and the bone mask image 46 generated in the process step of Step S106 so that the masked fat image 48 is generated (Step S107).

Then, the contour identification unit 76 generates the reduced skin mask image 50 based on the skin mask image 38 generated in the process step of Step S104 (Step S108).

Then, the masked body tissue image generation unit 78 executes a masking process which is based on the bone mask image 46 generated in the process step of Step S106 and the reduced skin mask image 50 generated in the process step of Step S108 so that the intermediate masked muscle image 52 is generated (Step S109).

Then, the contour identification unit 76 generates the comparison image 60 based on the masked fat image 48 generated in the process step of Step S107 (Step S110).

Then, the masked body tissue image generation unit 78 executes, with respect to the intermediate masked muscle image 52 generated in the process step of Step S109, a masking process which is based on the comparison image 60 generated in the process step of Step S110 so that the masked muscle image 62 is generated (Step S111).

Then, the masked body tissue image generation unit 78 stores the masked muscle image 62 generated in the process step of Step S111 into the masked body tissue image storage unit 80 (Step S112).

Then, the measurement image acquisition unit 72 confirms whether or not the process steps of from Step S102 to Step S112 have been executed for all of the measurement images 20 stored in the measurement image storage unit 70 (Step S113).

In this case, it is assumed that it has been confirmed that the process steps of from Step S102 to Step S112 have not been executed for all of the measurement images 20 stored in the measurement image storage unit 70 (Step S113: N). In this case, the process returns to the process step of Step S101.

Meanwhile, it is assumed that it has been confirmed that the process steps of from Step S102 to Step S112 have been executed for all of the measurement images 20 stored in the measurement image storage unit 70 (Step S113: Y). In this case, the body tissue mass estimation unit 82 estimates the skeletal muscle mass based on the plurality of masked muscle images 62 stored in the masked body tissue image storage unit 80 (Step S114), and the process illustrated in this process example is ended.

The execution order of the process steps of from Step S101 to Step S114 described above is not limited to the above-mentioned order, and the process steps may be executed in an order different from the above-mentioned order.

It should be noted that the present invention is not limited to the above-mentioned at least one embodiment.

For example, as the measurement image 20, an MRI image (for example, a T1-weighted image, a T2-weighted image, a diffusion weighted image, or the like) generated by an MRI apparatus may be used. Then, for a plurality of types of body tissues, filtering processes corresponding to those types of body tissues may be executed with respect to the MRI image so that the body tissue images associated with those types of body tissues are generated. Further, with respect to the body tissue image associated with a specific type of body tissue, a masking process which is based on the body tissue image associated with a different type of body tissue may be executed so that the masked body tissue image associated with this specific type of body tissue is generated.

While there have been described what are at present considered to be certain embodiments of the invention, it will be understood that various modifications may be made thereto, and it is intended that the appended claims cover all such modifications as fall within the true spirit and scope of the invention.

What is claimed is:

1. An image generation apparatus, comprising:
at least one processor; and
at least one memory device storing instructions which, when executed by the at least one processor, cause the at least one processor to perform operations comprising:
acquiring a measurement image indicating a measurement value of a predetermined physical quantity for a measurement target including a plurality of types of body tissues;
generating a body tissue image associated with each of the plurality of types of body tissues by executing, for the each of the plurality of types of body tissues, a filtering process corresponding to the each of the plurality of types of body tissues with respect to the measurement image; and
generating a masked body tissue image for a specific type of body tissue from the plurality of types of body tissues by executing, with respect to the body tissue image associated with the specific type of body tissue, a masking process which is based on the body tissue image associated with a different type of body tissue.

2. The image generation apparatus according to claim 1, wherein the operations further comprise:
identifying, based on the body tissue image, a contour of a body tissue in the body tissue image, wherein the generating the masked body tissue image comprises generating the masked body tissue image associated with the specific type of body tissue by executing, with respect to the body tissue image associated with the specific type of body tissue, a masking process which is based on the contour identified for a different type of body tissue.

3. The image generation apparatus according to claim 1, wherein the generating the body tissue image comprises generating the body tissue image associated with each of a muscle, a bone, and fat.

4. The image generation apparatus according to claim 3, wherein the generating the masked body tissue image comprises:
generating the masked body tissue image associated with the muscle by executing a masking process which is based on the body tissue image associated with the fat with respect to the body tissue image associated with the muscle.

5. The image generation apparatus according to claim 3, wherein the masked body tissue image generator is configured to generate the masked body tissue image associated with the muscle by executing a masking process which is based on the body tissue image associated with the fat and the body tissue image associated with the bone with respect to the body tissue image associated with the muscle.

6. The image generation apparatus according to claim 3, wherein the masked body tissue image generator is configured to generate the masked body tissue image associated with the fat by executing a masking process which is based on the body tissue image associated with the bone with respect to the body tissue image associated with the fat.

7. The image generation apparatus according to claim 1, further comprising a body tissue mass estimator configured to estimate, based on a plurality of the masked body tissue images which are generated for parts different from each other and are associated with the specific type of body tissue, a mass of the specific type of body tissue.

8. An image generation method, comprising:
acquiring a measurement image indicating a measurement value of a predetermined physical quantity for a measurement target including a plurality of types of body tissues;
generating a body tissue image associated with each of the plurality of types of body tissues by executing, for the each of the plurality of types of body tissues, a filtering process corresponding to the each of the plurality of types of body tissues with respect to the measurement image; and generating a masked body tissue image for a specific type of body tissue from the plurality of types of body tissues by executing, with respect to the body tissue image associated with the specific type of body tissue, a masking process which is based on the body tissue image associated with a different type of body tissue.

9. A non-transitory computer readable storage medium storing a program for causing a computer to execute:

acquiring a measurement image indicating a measurement value of a predetermined physical quantity for a measurement target including a plurality of types of body tissues;

generating a body tissue image associated with each of the plurality of types of body tissues by executing, for the each of the plurality of types of body tissues, a filtering process corresponding to the each of the plurality of types of body tissues with respect to the measurement image; and generating a masked body tissue image for a specific type of body tissue from the plurality of types of body tissues by executing, with respect to the body tissue image associated with the specific type of body tissue, a masking process which is based on the body tissue image associated with a different type of body tissue.

* * * * *